US 6,580,502 B1

(12) United States Patent  
Kuwabara

(10) Patent No.: US 6,580,502 B1
(45) Date of Patent: Jun. 17, 2003

(54) APPEARANCE INSPECTION METHOD AND APPARATUS

(75) Inventor: Masayuki Kuwabara, Mitaka (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 0 days.

(21) Appl. No.: 09/570,587

(22) Filed: May 12, 2000

(30) Foreign Application Priority Data

May 12, 1999 (JP) ............................................ 11-131408

(51) Int. Cl.[7] ........................ G01N 21/00; G01N 21/86; G06K 9/00
(52) U.S. Cl. ................ 356/237.3; 356/237.5; 250/559.41; 382/149
(58) Field of Search .................... 356/237.4, 237.5, 356/237.1, 237.3, 445; 348/125, 128, 126; 382/141, 144, 145, 149, 147; 250/559.43, 559.41, 216, 201.3, 578.1

(56) References Cited

U.S. PATENT DOCUMENTS

| | | | | |
|---|---|---|---|---|
| 5,218,193 A | * | 6/1993 | Miyatake | 250/201.4 |
| 5,587,832 A | * | 12/1996 | Krause | 250/216 |
| 5,726,756 A | * | 3/1998 | Aki et al. | 250/559.27 |
| 5,822,055 A | * | 10/1998 | Tsai et al. | 250/559.39 |
| 6,034,780 A | * | 3/2000 | Kato | 250/548 |
| 6,078,386 A | * | 6/2000 | Tsai et al. | 356/237.1 |
| 6,248,988 B1 | * | 6/2001 | Krantz | 250/201.3 |
| 6,288,780 B1 | * | 9/2001 | Fairley et al. | 356/237.1 |
| 6,399,935 B1 | * | 6/2002 | Jovin et al. | 250/216 |

FOREIGN PATENT DOCUMENTS

EP 0871052 3/1998

OTHER PUBLICATIONS

Patent Abstract of Japan No. 04236307A, Published Aug. 25, 1992, NEC Corp.
Patent Abstract of Japan No. 05041430A, Published Feb. 19, 1993, NEC Corp.
Patent Abstract of Japan No. 07200779A, Published Aug. 4, 1995, Fujitsu Ltd.
Patent Abstract of Japan No. 08005569A, Published Jan. 12, 1996, Matsushita Electronic Corp.

* cited by examiner

Primary Examiner—Zandra V. Smith
Assistant Examiner—Gordon J Stock
(74) Attorney, Agent, or Firm—Christie, Parker & Hale, LLP

(57) ABSTRACT

An appearance inspection method, and an-apparatus therefor, capable of acquiring high quality in-focus images throughout the entire zone of an inspection object, by acquiring simultaneously two images on different focal planes by.using two TDI cameras (23, 24) having a sensitivity in a respective wavelength band ($\lambda 1, \lambda 2$), slicing the images in accordance with a region division that is defined in advance, and comparing the images. According to another aspect of this invention, the images are acquired by a confocal microscope constituted by disposing two corresponding pin-holes (37, 38), on the illumination side of a microscope and its light reception side, and one TDI camera (40).

13 Claims, 5 Drawing Sheets

APPEARANCE INSPECTION METHOD AND APPARATUS

BACKGROUND OF THE INVENTION

1. Field of the Invention

The present invention relates to a pattern inspection technology, that is, a technology that can.be effective when applied to fault inspection of a pattern on a semiconductor wafer.

2. Description of the Related Art

According to a typical conventional pattern inspection method, multi-value images are acquired while an inspection object is being scanned continuously in an x direction by an image acquiring unit comprising the, combination of an optical microscope with an imaging device such as a TDI (Time Delay Integration) camera, and these images are then stored in an image data storing unit such as a memory. Gray levels of adjacent dies are compared in a pixel unit in parallel with the operation described above, and a pixel having a gray level difference, that exceeds a predetermined reference value, is recognized as a pixel that may indicate faults. The appearance inspection of the entire surface of a semiconductor wafer is conducted by continuously executing these operations.

Acquisition of a high quality image is of utmost importance in order.to achieve high precision inspection in the appearance inspection. The high quality image must have sufficient bright-and-dark contrast, precise focus on the inspection object, and so forth.

An appearance inspection.apparatus "KLA-2135" of KLA Co., U.S.A., as a typical example of-the appearance inspection apparatuses that are now commercially available, is equipped with an x-y-z stage capable of moving relatively to a microscope that is kept fixed. This x-y-z stage is controlled in the z direction on the basis of a feedback signal from an auto-focus mechanism so that the gap between the surface of a semiconductor wafer and an objective lens is always constant. Therefore, the altitude in the z direction, that is judged as being in "just-in-focus" by the auto-focus mechanism, is traced during scanning in the x direction.

In the chip structure of a semiconductor device, however, structures having different surface altitudes such as a cell portion, a peripheral circuit portion, etc, are fabricated. For this reason, the rays of light are not always in just focus on the chip surface even when the auto-focus mechanism judges the focusing state as "just-in-focus". When the semiconductor devices are inspected with a high level of accuracy through chip comparison, it has therefore become difficult in recent years to acquire a high quality image using the appearance inspection apparatus having the construction described above.

In the case of a DRAM as a typical memory device, the chip can be divided broadly into a cell portion and a peripheral circuit portion. In order to secure the capacitance at the cell portion, the cell portion tends to extend upward with miniaturization of the device size in comparison with the peripheral circuit portion.

FIG. 4A of the accompanying drawings is a top plan view showing an example of a known semiconductor device, and FIG. 4B is a sectional view taken along a line IV—IV of FIG. 4A. As shown in these drawings, an altitude difference exists between the cell portion and the peripheral circuit portion, and this difference reaches nearly 1 micron in certain devices.

The appearance inspection apparatus desirably has the capability of detecting faults with a high level of accuracy in both of the cell portion and the peripheral circuit portion.

FIG. 5 is an explanatory view useful for explaining a scanning operation in the transverse direction on the upper surface of the semiconductor device shown in FIG. 4A. In FIG. 5, a reference symbol W represents the width that is covered by the one-time scanning operation by the TDI camera. When scanning is conducted in such a fashion that the two different regions, i.e., the cell portion and the peripheral circuit portion, are contained at the upper and lower portions in the figure of the same scanning range as represented by the region 1 the auto-focus mechanism can place the focus on only one of them. In other words, the other region is subjected to a comparative inspection using an image that is acquired under an unfocused state and has low image quality.

Another problem of the focusing operation is that the image is acquired by the TDI camera. The output of the TDI camera is analogous to that of a one-dimensional line sensor, and it outputs an apparently one-dimensional image information. However, the TDI camera has practically a two-dimensional light reception surface, and makes up for insufficiency of light power resulting from high-speed scanning by serially moving the charge to adjacent pixels in synchronism with the relative movement of the inspection object so as to increase the charge storage quantity. Therefore, while a certain region of the inspection object is being moved in the direction of integration of the TDI camera, a predetermined distance must be kept between the light reception surface of the TDI camera and the image formation surface in order to acquire a high quality image. However, when scanning is made in such a fashion as to bridge over the altitude difference between the cell portion an d the peripheral circuit portion as represented by the region 2 in FIG. 5, the auto-focus mechanism moves the wafer, which is the inspection object, in the z direction so as to place the focus on the boundary. In other words, the overlapping image of the image, which is in focus, and the image, which is out of focus, is outputted in the proximity of the altitude difference portion as represented by the region 2 with the result of the drop of image quality. The region in which deterioration of image quality occurs becomes greater as the number of integration stages by the TDI camera increases. Therefore, the method that makes up for insufficiency of light power by increasing the number of integration stages becomes unfeasible. For these two reasons, the images having the just-in-focus cannot be acquired in all the regions of the entire surface of the chip and eventually, it has been difficult to improve the fault detection sensitivity.

The appearance inspection apparatus with a confocal microscope equipped with an electric scanning table, that is described in European Unexamined Patent Publication No. 0871052 ("Microscope with Movable. Scanning Table") laid open on Oct. 14, 1998, has a much smaller depth of focus than ordinary microscopes because the confocal microscope is employed. In inspecting only a region having a specific altitude, this appearance inspection apparatus can obtain excellent effects because the depth of focus is extremely small, while making other regions difficult to observe. In consequence, this appearance inspection apparatus can drastically improve the image contrast of the inspection region and eventually, can inspect the appearance with high sensitivity. However, when it is desired to inspect only the outermost surface of both region of an inspection object having a large altitude difference between, for example, the cell portion and the peripheral circuit portion, this appearance inspection apparatus can naturally place the focus on only either one of these portions and can hardly acquire effective image information of the other portion due to the confocal effect. Therefore, when both of the cell portion and the peripheral circuit portions are to be inspected, it is necessary to conduct the full surface inspection by placing the focus on the cell portion and then to conduct once again the full surface inspection by placing the focus on the peripheral circuit portion. Thus, inspection efficiency drops.

SUMMARY OF THE INVENTION

In view of the problems with the prior art technologies described above, it is an object of the present invention to provide an appearance inspection method, and an apparatus therefor, capable of acquiring high quality images having a precise focus over the entire zone of an inspection object.

Typical aspects of the invention described in this application may be briefly summarized as follows.

The appearance inspection apparatus of the present invention combines a light source having two or more wavelength bands with a microscope having chromatic aberration.so that rays of light of one of the wavelength bands can always place the focus on the surface of the inspection object even when the inspection object has the altitude difference in an area between, for example, the cell portion and the peripheral circuit portion. In this way, the appearance inspection apparatus can acquire high quality images having a precise focus throughout all the zones of the inspection object.

According to one aspect of the present invention for accomplishing this object, the present invention provides an appearance inspection method, and an apparatus therefor, that use two TDI cameras each having a sensitivity in only a specific wavelength band in order to simultaneously acquire two images on different focal planes, and slice the images for comparative inspection in accordance with a region division that is defined in advance.

According to another aspect of the present invention, there are provided an appearance inspection method, and an apparatus therefor, that acquire images by using a co-focal microscope having two corresponding pin-hole arrays on the illumination side and on the light reception side, and one TDI camera.

An explanation will be given in further detail. According to one aspect of the present invention, in an appearance inspection method for detecting a fault of an inspection object by comparing an image that is obtained by imaging a pattern arranged on the inspection object in a predetermined direction with an image of a pattern arranged at a corresponding position of other inspection object, the present invention provides an appearance inspection method, and an apparatus therefor, that comprise the steps of radiating rays of light by illumination means capable of radiating rays of light having at least two wavelength bands; changing the direction of the rays of light from the illumination mean by a beam splitter; causing the ray of light, the direction of which is so changed, to focus on the surface of the inspection object through an optical system having such chromatic aberration as to place the focus at a position corresponding to each wavelength band; separating the rays of light of the two wavelength bands reflected from the surface of the inspection object into two directions by a half mirror through an optical system and a beam splitter; causing one of the rays of light so separated to travel towards a first wavelength selection means and the other ray of light so separated to travel towards a second wavelength selection means; allowing one of the rays of light of at least two wavelength bands to pass through the first wavelength selection means and the other of the rays of light of the other wavelength band to pass through the second wavelength selection means; receiving the rays of light passing through the first and second wavelength selection means by at least two imaging means, respectively, so as to thereby image an image of a pattern region for each wavelength band; synthesizing the taken image data so taken; and detecting a fault on the inspection object on the basis of the comparison result obtained by comparing the image of each region of the synthetic image with an image of a pattern arranged at a corresponding position of other inspection object.

Imaging is conducted using a TDI camera.

The optical system having chromatic aberration comprises a plurality of objective lenses each having a different degree of chromatic aberration.

In an appearance inspection method for detecting.a fault of an inspection object by comparing an image acquired by imaging a pattern arranged in a predetermined direction on the inspection object with an image arranged at a corresponding position of another inspection object, the second embodiment of the present invention provides an appearance inspection method, and an apparatus therefor, that comprise the steps of radiating rays of light by illumination means capable of radiating rays of light having at least two waveband lengths; causing the rays of light from the illumination means to pass through a first pin-hole array; changing the direction of the ray of light passing through the first pin-hole array by a beam splitter; causing the ray of light, the direction of which is so changed, to focus on the surface of the inspection object through an optical system having such chromatic aberration as to place the focus on a position corresponding to each wavelength band; separating the ray of light reflected from the inspection object into two directions by a beam splitter; causing one of the rays of light so separated to travel towards a first pin-hole array and the other of the rays of light to travel towards a second pin-hole array constituting a confocal microscope together with the first pin-hole array; receiving the ray of light passing through the second pin-hole array by imaging means to image an image of a pattern region; and detecting a fault of the inspection object on the basis of the comparison result obtained by comparing the image with an image of a pattern arranged at a corresponding position of other inspection object.

In this embodiment, too, imaging is conducted using the TDI camera.

The optical system having chromatic aberration comprises a plurality of objective lenses each having a different degree of chromatic aberration when images are acquired inside the device having the altitude difference such as between the cell portion and the peripheral circuit portion during a scanning operation of optical recognition means, the present invention allows each ray of light having a different wavelength band to always begin just-in-focus on each region. Since the image so acquired is a high quality image having a precise focus in each region, a high-precision fault detection capability can eventually be provided.

BRIEF DESCRIPTION OF THE DRAWINGS

The above object and features of the present invention will be more apparent from the following description of the preferred embodiments when read with reference to the accompanying drawings; wherein.

DESCRIPTION OF THE PREFERRED EMBODIMENTS

Embodiment 1

Figure 1:
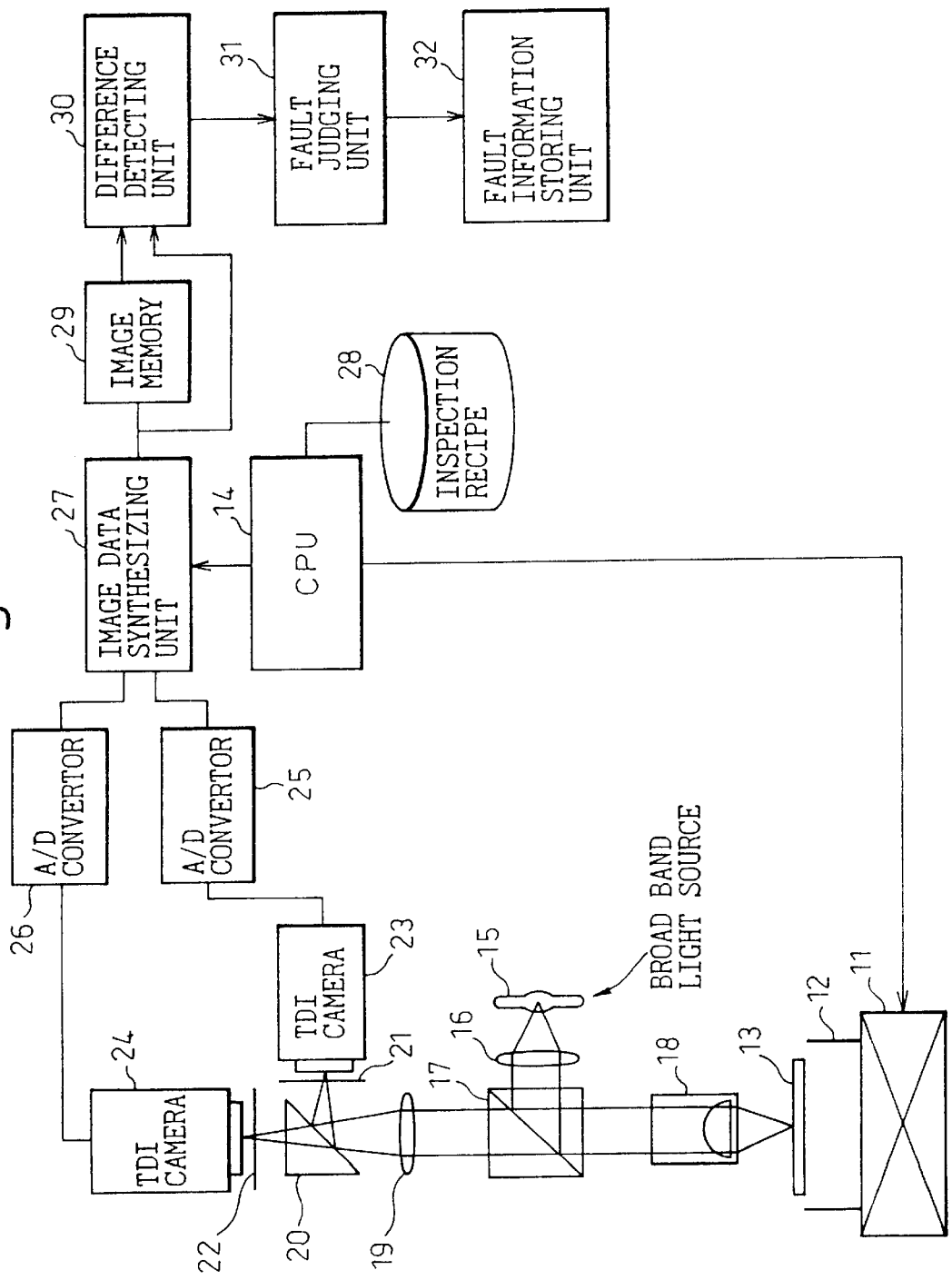
FIG. 1 is a block diagram showing a construction of a fault inspection apparatus according to the first embodiment of the present invention.

FIG. 1 is a block diagram showing the construction of an appearance inspection apparatus according to the first embodiment of the present invention. In the drawing, reference 11 denotes a high precision x-y stage, 12 a wafer chuck, 13 a semiconductor wafer, 14 a CPU, 15 a light source, 16 a collector lens, 17 a beam splitter, 18 an objective lens having chromatic aberration left unremoved, 19 a condenser lens, 20 a half mirror, 21 and 22 filters, 23 and 24 TDI cameras, 25 and 26 A/D converters, 27 an image data synthesizing unit, 28 a data base, 29 an image memory, 30 a difference detecting unit, 31 a fault judging unit, and 32 a fault information storing unit.

Next, the operation will be explained. The wafer chuck 12 is fitted on the high precision x-y stage 11 that can freely move the in x and y directions. The wafer 13 is vacuum sucked onto the wafer chuck 12. The x-y stage 11 is controlled by the CPU 14 and is relatively moved with respect to the microscope, thereby scanning the entire surface of the wafer. The rays of light emitted from the light source 15, that has a broadband light emission wavelength, are converted to parallel rays of light by the collector lens 16, are then bent downward by the beam splitter 17, pass through the objective lens 18 and uniformly illuminate the wafer 13 which is an inspection object (with Kohler illumination). White rays of light reflected from the surface of the semiconductor wafer 13 pass again through the objective lens 18 and the beam splitter 17, pass further through the condenser lens 19, and are divided into two optical paths by the half mirror 20. The filters 21 and 22 respectively capable of passing, different wavelength bands are provided to these two optical paths. The rays of light passing through the respective filters are subjected to image formation by optical imaging means such as the TDI cameras 23 and 24. The image signals outputted from the two TDI cameras 23 and 24 are converted to multi-value digital signals by the A/D converters 25 and 26 connected in series with the TDI cameras, respectively, and are then sent to the image data synthesizing unit 27. The image data synthesizing unit 27 is controlled by the CPU 14. This image data synthesizing unit 27 eventually acquires one synthetic image slicing the image of a cell portion from the digital image that is in focus with the cell portion, among the digital images sent from the two A/D converters 25 and 26 on the basis of region information registered into an inspection recipe stored in advance in the data base 28, slicing the image of the peripheral circuit portions from the images, that are in focus with other peripheral circuit portion, and synthesizing these images This synthetic image is thereafter subjected to fault detection by a method similar to the method that is employed by an ordinary appearance inspection apparatus, that is, image comparison. In other words, the image outputted from the image data synthesizing unit is once stored in the image memory 29 capable of storing the image signals for at least one die, and is delayed by a delay time of one die. This delay image and the image of the adjacent die, that is outputted from the image data synthesizing unit without the delay, are sent to the difference detecting unit 30. When the difference detecting unit 30 calculates the difference of the gray level between the corresponding pixels, a difference image is formed. The difference image is sent next to the fault judging unit 31. The pixel that exceeds a threshold value defined in advance is recognized as a fault pixel, and the information of a fault occurrence position, and so forth, is stored in the fault information storing unit 32. When the series of operations described above are executed for the entire surface of the wafer, a final fault map is obtained, and this fault map is outputted to a monitor, not shown in the drawings.

It is of importance in this embodiment of the present invention that white rays of light reflected from the semiconductor wafer, that has an altitude difference between the cell portion and the peripheral circuit portion, are allowed to place the focus on different positions in the z direction for the respective wavelength bands, by using a microscope that intentionally leaves chromatic aberration unremoved. This will be explained with reference to FIG. 2.

Figure 2:
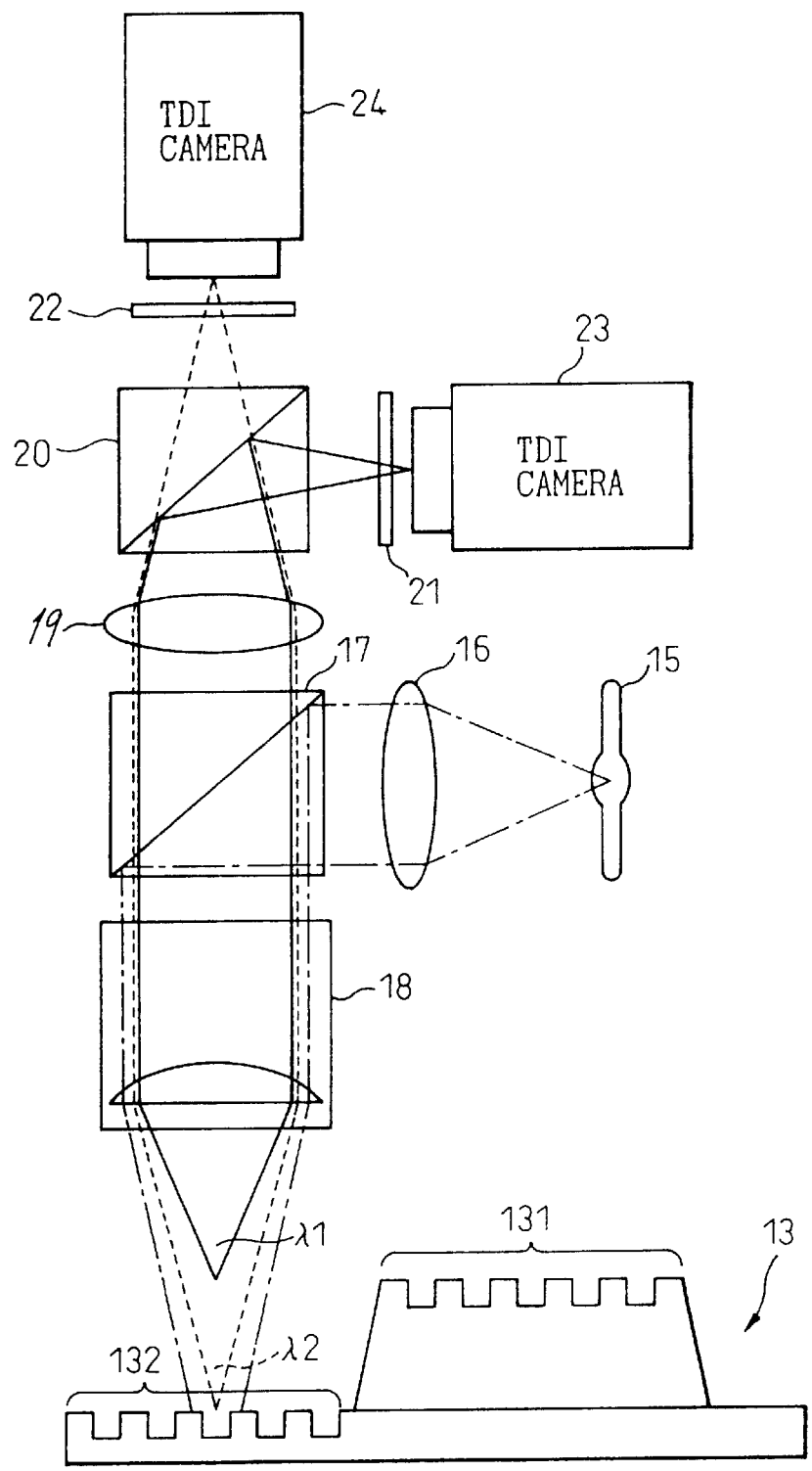
FIG. 2 is a schematic view showing a construction of an optical system in FIG. 1.

FIG. 2 is a detailed explanatory view of the optical system shown in FIG. 1 In FIG. 2, the same reference numeral is used to identify the same constituent element as in FIG. 1. The ray of light of a wavelength band $\lambda 1$ is allowed to place the focus on the surface of the cell portion 131, and the ray of light of a wavelength band $\lambda 2$ is allowed to place the focus on the surface of the peripheral circuit portion 132. Because the filters 21 and 22 are disposed immediately before the TDI cameras 23 and 24 as the optical imaging means, respectively, the images that are in focus can be selectively inputted. As a result, a high quality image can be acquired.

It is difficult in an ordinary optical design stage to continuously and freely change the chromatic aberration. In order to cope with the altitude difference having an arbitrary height, therefore, an optical system having several stages, that ranges from a small degree of chromatic aberration to a high degree, is employed, and the wavelength characteristics of the filters 21 and 22 are changed for in order to perform the remaining fine adjustments so that the rays of light having respective wavelengths have their focal points at the upper and lower positions of the altitude difference.

To perform the remaining fine adjustments, each of the filters 21 and 22 may have a disc shape, and on the disc, there may be a plurality of sub filters having different wavelength characteristics. The disc may be rotated by a motor so as to use a desired sub filter to pass light having desired wavelengths. It should be noted that the configuration of the filter 21 should be the same as the configuration of the filter 22.

The objective lens 18 comprises a plurality of objective lenses having different degrees of chromatic aberration to each other to obtain a desired chromatic aberration characteristic.

Embodiment 2

Depending on the amount of the chromatic aberration of the objective lens 18 and the wavelength band of the light that passes through the filters 21 and 22, the altitude difference applicable to the present invention is determined. In other words, the larger the chromatic aberration of the objective lens 18, the larger the applicable altitude difference of the subject such as the semiconductor wafer, so that, by using the sub filters, various types of devices from the one having a smaller altitude difference to the one having the maximum applicable altitude difference can be inspected.

Figure 3:
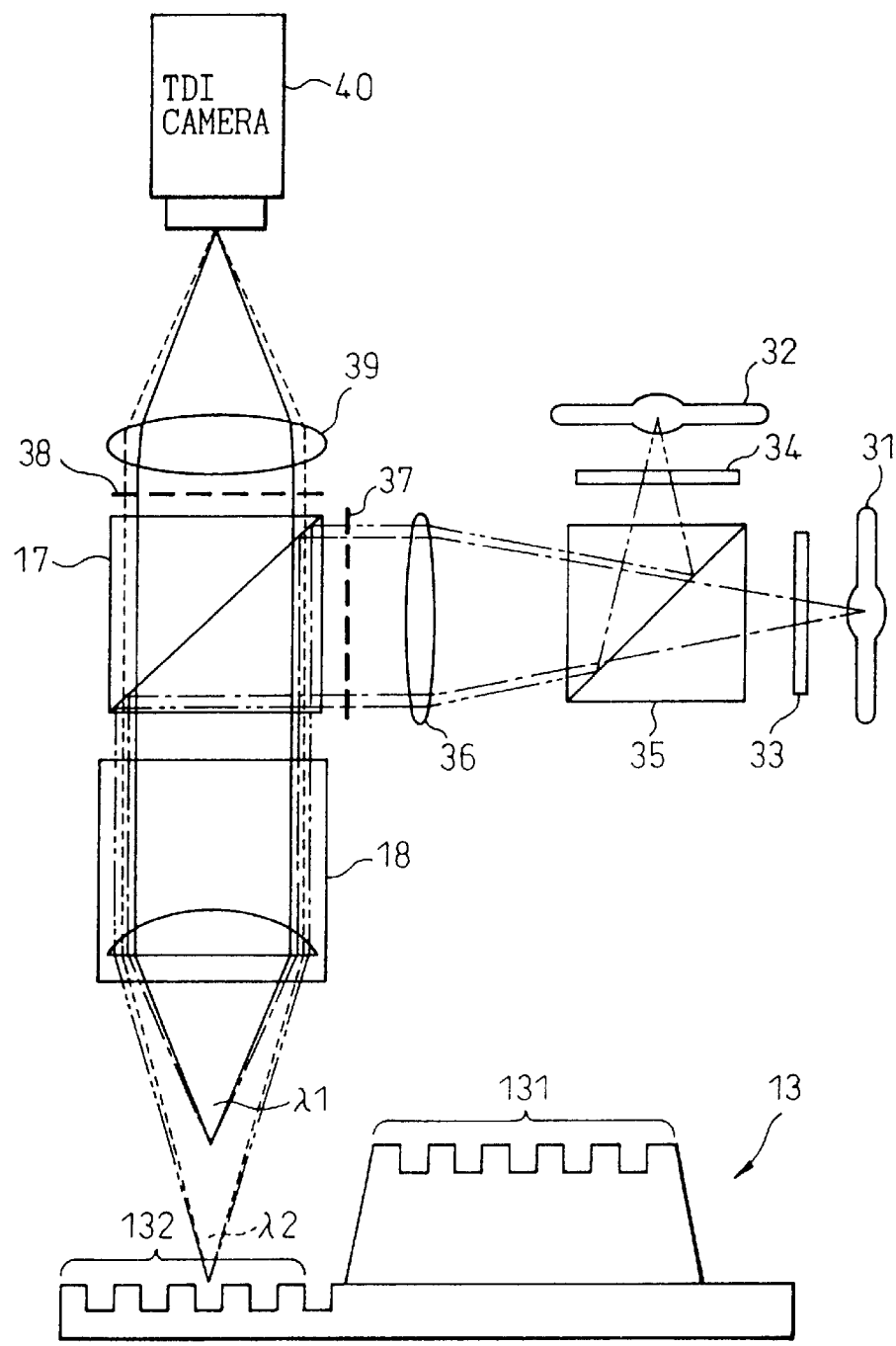
FIG. 3 is a schematic view showing a construction of an optical system of a fault inspection apparatus according to the second embodiment of the present invention.
Figure 4A:
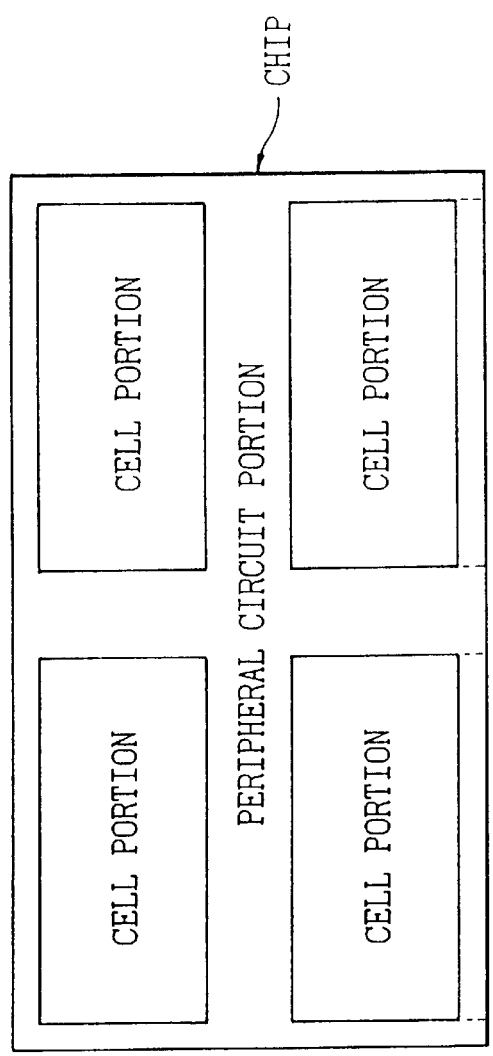
FIG. 4A is a top view showing a known semiconductor device.
Figure 4B:
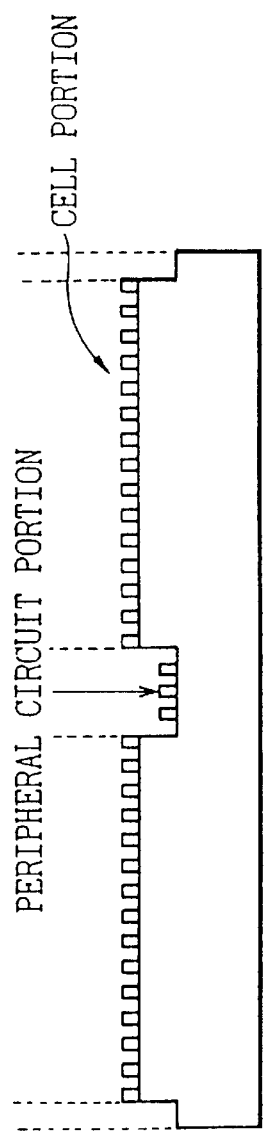
FIG. 4B is a sectional view of the semiconductor device.
Figure 5:
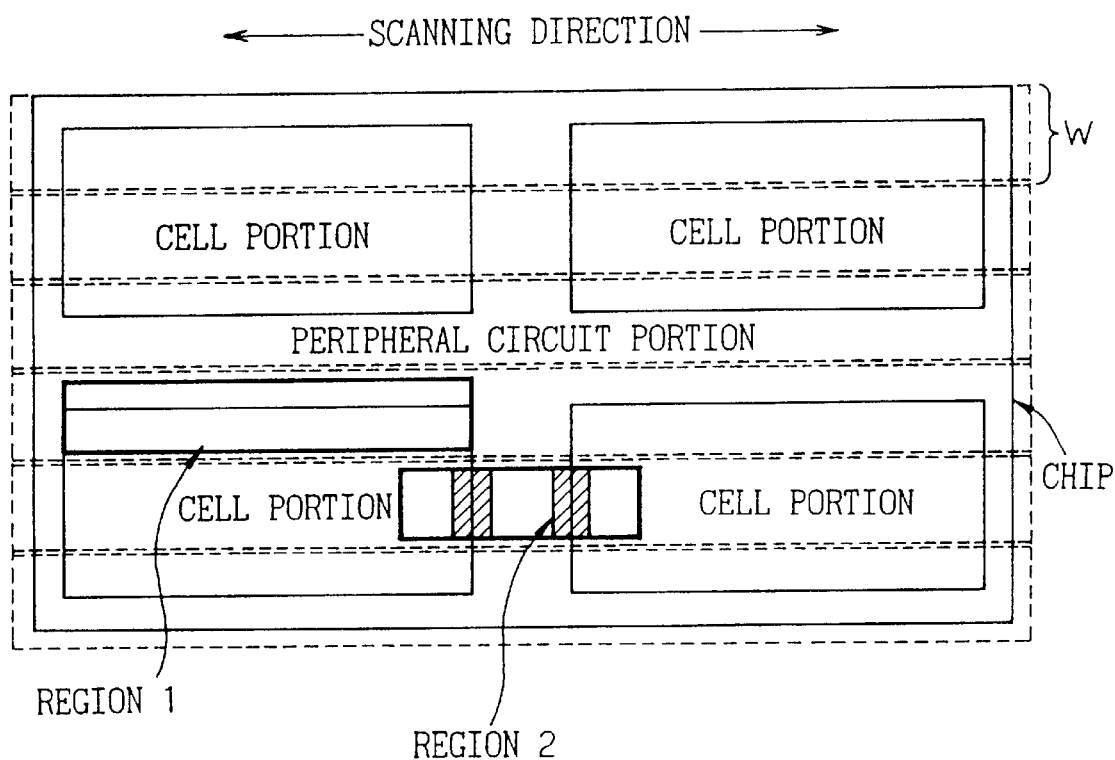
FIG. 5 is an explanatory view useful for explaining the problems to be solved by the present invention when a semiconductor device is scanned.

FIG. 3 shows the construction of an optical system of an appearance inspection apparatus according to the second embodiment of the present invention. In FIG. 3, the same reference numeral is used to identify the same constituent element as in FIG. 1. The microscope shown in FIG. 3 is of an improved type of the microscope disclosed, in European Unexamined Patent Publication No. 0871052 with an electric scanning table. This microscope accomplishes a confocal microscope by disposing two pin-hole arrays corresponding to each other on the optical paths on the illumination side and on the light reception side, respectively, and scanning relatively the inspection object such as the semiconductor wafer with respect to the optical imaging means that is kept fixed. In other words, this embodiment modifies the light source portion of this confocal microscope to a two-wavelength configuration.

In FIG. 3, reference numerals 31 and 32 denote the light sources, 33 and 34 the filters, 35 the half mirror, 36 the condenser lens, 37 and 38 the pin-hole arrays, 39 the condenser lens, and 40 denotes the TDI camera.

A two-color light source having two different wavelengths is realized by either one of using different filters or using light sources having different light emission wavelengths, or using them in combination. In the example shown in FIG. 3, the light source 31 that emits rays of light inclusive of the ray of light of a wavelength $\lambda 1$ and the light source 32 that emits the rays of light inclusive of the ray of light of a wavelength $\lambda 2$ are prepared. The filter 33 allows the passage of the ray of light of the wave length $\lambda 1$ and the filter 34 allows the passage of the ray of light of the wavelength $\lambda 2$. The half mirror 35 synthesizes these rays of light and accomplishes the light sources of the two colors.

Next, the operation will be explained. The ray of light from the half mirror 35 is converted to parallel rays of light by the collector lens 36 and then passes through the pin-hole array 37. The pin-hole array 37 is a shading plate with pin-holes arranged in predetermined gaps. Only the rays of light passing through the holes reach the surface of the inspection object through the beam splitter 17 and through the objective lens 18. The rays of light reflected from the surface of the inspection object reach a pin-hole array 38 again through the objective lens 18 and through the beam splitter 17. This pin-hole array 38 includes holes at the positions corresponding to the holes of the pin-hole array 37. The higher the illumination density on the surface of the inspection object or in other words, the closer the surface of the inspection object is to the image surface of the pin-hole array 37, the greater becomes the quality of the rays of light that can pass through the pin-hole array 38. The confocal microscope is accomplished on the basis of this principle.

In this embodiment, the light sources 31 and 32 having two wavelengths $\lambda 1$ and $\lambda 2$ and the objective lens 18 having chromatic aberration are combined with one another. The image surface of the pin-hole array 37 is formed at a different position in the z direction in accordance with the wavelengths of the light sources.

Considering the ray of light having the wavelength $\lambda 1$ by way of example, since the image surface of the pin-hole array 37 is formed at the height of the surface of the cell portion 131, the reflected ray of light having this wavelength passes most efficiently through the pin-hole array 38 when the surface of the inspection object exists near this height. Consequently, a bright image is formed by the TDI camera 40. On the other hand, while the same ray of light illuminates the peripheral circuit portion 132, illumination is effected in a broader range than the illumination of the surface of the cell portion because it is not the image surface of the pin-hole array 37. However, the reflected ray of light is greatly limited by the pin-hole array 38 and does not reach the TDI sensor 40, and the image becomes extremely dark. In consequence, the ray of light having the wavelength $\lambda 1$ can transmit only the image information that is in focus at the height of the cell portion to the TDI camera.

On the other hand, the ray of light having the wavelength $\lambda 2$ can transmit only the image information that is in focus at the height of the peripheral circuit portion 132 to the TDI camera 40 because the image surface of the pin-hole array 37 is formed at the height of the peripheral circuit portion 132. Therefore, in the appearance inspection apparatus using the confocal microscope having this construction, the image having the focus on both of two different heights of the inspection object having such heights can be inputted without using the image data synthesizing unit shown in FIG. 1.

Some typical advantages and effects of this invention may be briefly summarized as follows.

The present invention can acquire a high quality image having the focus on each region of the inspection object having a large altitude difference between the cell portion and the peripheral circuit portion as has often been observed in memory devices such as DRAMs. Therefore, the present invention can drastically improve the inspection sensitivity in the appearance inspection through image comparison.

What is claimed is:

1. An appearance inspection method for detecting a fault of an inspection object having pattern regions by comparing an image acquired by imaging said pattern regions arranged in a predetermined direction on said inspection object with an image of a pattern arranged at a corresponding position of another inspection object, comprising the steps of:

radiating rays of light by illumination means for radiating the rays of light having at least two wavelength bands;

changing the direction of the rays of light from said illumination means by a beam splitter;

focusing said rays of light, the direction of which is so changed on the surface of said inspection object, through a single fixed optical system having such chromatic aberration as a to focus the rays of light on positions corresponding to said wavelength bands;

separating the rays of light of said two wavelength bands reflected from the surface of said inspection object into two directions by a half mirror through said optical system and through said beam splitter and causing one of the rays of light so separated to travel towards first wavelength selection means and the other towards second wavelength selection means;

allowing one of the rays of said at least two wavelength bands to pass through said first wavelength selection means and the other of the rays of light of at least two wavelengths bands to pass through said second wavelength selection means;

receiving the rays of light passing through said first and second wavelength selection means by at least two imaging means, respectively, and simultaneously imaging the image of said pattern regions by said wavelength bands, respectively;

synthesizing the taken image data; and detecting a fault of said inspection object by comparing the image of each region of said synthetic image with the image of a pattern arranged at a corresponding position of other inspection object.

2. An appearance inspection method according to claim 1, wherein said imaging step is conducted by using a TDI camera.

3. An appearance inspection method according to claim 1, wherein said optical system having chromatic aberration comprises a plurality of objective lenses each having a different degree of chromatic aberration.

4. An appearance inspection apparatus for detecting a fault of an inspection object having patter regions by imaging said pattern regions arranged in a predetermined direction on said inspection object with the image of a pattern arranged at a corresponding position of other inspection object, comprising:

illumination means for radiating rays of light having at least two wavelength bands;

a beam splitter for changing the direction of the ray of light from said illumination means;

a single fixed optical system having chromatic aberration such that the rays of light the direction of which is changed by said beam splitter have the focus on the surface positions of said inspection object corresponding to the wavelength bands;

a half mirror for separating the ray reflected from the surface of said inspection object and passing through said optical system and through said beam splitter into two directions;

first wavelength selection means for receiving one of the rays or light separated by said half mirror and allowing one of the rays of said at least two wavelength bands to pass therethrough;

second wavelength selection means for receiving the other of the rays of light separated by said half mirror and allowing the other of the rays of said at least two wavelength bands, to pass therethrough;

at least two imaging means for receiving the rays of light passing through said first and second wavelength selection means, and simultaneously forming images of the surfaces of said inspection object by said wavelength bands, respectively image data synthesizing means for synthesizing the outputs of said imaging means; and fault detection means for detecting a fault of said inspection object on the basis of the comparison result obtained by comparing the image of each region obtained from said image data synthesizing means with the image of other pattern arranged at a corresponding position of other inspection object.

5. An appearance inspection apparatus according to claim 4, wherein said imaging means is a TDI camera.

6. An appearance inspection apparatus according to claim 4, wherein said optical system having said chromatic aberration comprises a plurality of objective lenses each having a different degree of chromatic aberration.

7. An appearance inspection method for detecting a fault of an inspection object having pattern regions by comparing an image acquired by imaging said pattern regions arranged in a predetermined direction on said inspection object with an image of a pattern arranged at a corresponding position of other inspection object, comprising the steps of:

radiating rays of light by illumination means capable of radiating rays of light having at least two wavelength bands;

causing the rays of light from said illumination means to pass through a first pin-hole array;

changing the direction of the rays of light passing through said first pin-hole array by a beam splitter;

focusing the rays of the light passed through said first pin-hole array on said pattern regions of said inspection object through a single fixed optical system having such chromatic aberration as to focus the rays of light on said pattern regions corresponding to said wavelength bands;

separating the rays of light reflected from the surface of said inspection object into two directions by said beam splitter through said optical system, and causing one of the rays of light so separated to travel towards said first pin-hole array and the other of the rays of light to travel towards a second pin-hole constituting a co-focal microscope with said first pin-hole array;

receiving the rays of light passing through said second pin-hole array by imaging means and simultaneously imaging the images of said pattern regions, respectively; and detecting a fault of said inspection object on the basis of the comparison result obtained by comparing the image so imaged with an image of a pattern arranged at a corresponding position of other inspection object.

8. An appearance inspection method according to claim 7, wherein said imaging step is conducted by using a TDI camera.

9. An appearance inspection method according to claim 7, wherein said optical system having said chromatic aberration comprises a plurality of objective lenses each having a different degree of chromatic aberration.

10. An appearance inspection apparatus for detecting a fault of an inspection object having pattern regions by imaging said pattern regions arranged in a predetermined direction on an inspection object with an image of a pattern arranged at a corresponding position of other inspection, comprising;

illumination means capable of radiating rays of light having at least two wavelength bands;

a first pin-hole array for allowing the rays of light from said illumination means to pass therethrough;

a beam splitter for changing the direction of the rays of light passing through said first pin-hole array;

a single fixed optical system having such chromatic aberration as to allow the rays of light passed through said first pin-hole array to focus on said pattern regions corresponding to said wavelength bands of said inspection object, respectively;

a second pin-hole array constituting a confocal microscope with said first pin-hole array;

imaging means for simultaneously forming images of said pattern regions by receiving the rays of light passing through said second pin-hole array; and fault detection means for detecting a fault of said inspection object on the basis of the comparison result obtained by comparing the image acquired from said imaging means with an image of a pattern arranged at a corresponding position of other inspection object.

11. An appearance inspection apparatus according to claim 10, wherein said imaging means is a TDI camera.

12. An appearance inspection apparatus according to claim 10, wherein said optical system having said chromatic aberration comprises a plurality of objective lenses each having a different degree of chromatic aberration.

13. An appearance inspection method for detecting a fault of an inspection object having pattern regions by comparing an image acquired by imaging said pattern regions arranged in a predetermined direction on said inspection object with an image of a pattern arranged at a corresponding position of another inspection object, comprising the steps of:

radiating rays of light by illumination means for radiating the rays of light having at least two wavelength bands;

changing the direction of the rays of light from said illumination means by a beam splitter;

focusing said rays of light, the direction of which is so changed on the surface of said inspection object, through an optical system having such chromatic aberration as to focus the rays of light on positions corresponding to said wavelength bands; separating the rays of light of said two wavelength bands reflected from the surface of said inspection object into two directions by a half mirror through said optical system and through said beam splitter and causing one of the rays of light so separated to travel towards first wavelength selection mean and the other towards second wavelength selection means;

allowing one of the rays of said at least two wavelength bands to pass through said first wavelength selection means and the other of the rays of light of at least two wavelengths bands to pass through said second wavelength selection means;

receiving the rays of light passing through said first and second wavelength selection means by at least two imaging means, respectively, and simultaneously imaging the image of said pattern regions by said wavelength bands, respectively;

synthesizing the taken image data; and detecting a fault of said inspection object by comparing the image of each region of said synthetic image with the image of a pattern arranged at a corresponding position of other inspection object.

* * * * *

UNITED STATES PATENT AND TRADEMARK OFFICE
CERTIFICATE OF CORRECTION

PATENT NO. : 6,580,502 B1
DATED : June 17, 2003
INVENTOR(S) : Masayuki Kuwabara

It is certified that error appears in the above-identified patent and that said Letters Patent is hereby corrected as shown below:

<u>Title page,</u>
Item [57], ABSTRACT, change "an-apparatus" to -- an apparatus --; and change "by.using" to -- by using --.

<u>Column 8,</u>
Line 48, delete "a".

<u>Column 9,</u>
Line 14, change "patter" to -- pattern --.
Line 33, change "or" to -- of --.
Line 39, change "bands," to -- bands --.
Line 44, change "respectively" to -- respectively; --

<u>Column 11,</u>
Line 18, change "mean" to -- means --.

Signed and Sealed this

Twenty-seventh Day of July, 2004

JON W. DUDAS
*Acting Director of the United States Patent and Trademark Office*